US009770532B2

(12) United States Patent
Pertici

(10) Patent No.: US 9,770,532 B2
(45) Date of Patent: Sep. 26, 2017

(54) BONE IMPLANT MATRIX AND METHOD OF PREPARING THE SAME

(75) Inventor: Gianni Pertici, Lugaggia (CH)

(73) Assignee: INDUSTRIE BIOMEDICHE INSUBRI S/A, Mezzovico (CH)

( * ) Notice: Subject to any disclaimer, the term of this patent is extended or adjusted under 35 U.S.C. 154(b) by 224 days.

(21) Appl. No.: 13/128,062

(22) PCT Filed: Dec. 15, 2009

(86) PCT No.: PCT/IB2009/007759
§ 371 (c)(1),
(2), (4) Date: May 6, 2011

(87) PCT Pub. No.: WO2010/070416
PCT Pub. Date: Jun. 24, 2010

(65) Prior Publication Data
US 2011/0218646 A1    Sep. 8, 2011

(30) Foreign Application Priority Data

Dec. 19, 2008  (CH) ........................................ 1997/08

(51) Int. Cl.
*A61F 2/28*  (2006.01)
*A61L 27/44*  (2006.01)
*A61L 27/36*  (2006.01)

(52) U.S. Cl.
CPC ........... *A61L 27/44* (2013.01); *A61L 27/3608* (2013.01); *A61L 2430/02* (2013.01)

(58) Field of Classification Search
CPC ....................................................... A61F 2/28

USPC ........... 623/11.11, 23.6–23.63; 523/113–116; 424/422, 423, 426, 484–486; 514/781, 514/944
See application file for complete search history.

(56) References Cited

U.S. PATENT DOCUMENTS

| | | | |
|---|---|---|---|
| 6,569,200 B2 * | 5/2003 | Wolfinbarger et al. .... | 623/13.11 |
| 6,998,134 B2 * | 2/2006 | Schmidmaier .......... | A61L 27/34 424/422 |
| 2002/0183858 A1 * | 12/2002 | Contiliano et al. ........ | 623/23.76 |
| 2004/0265385 A1 * | 12/2004 | West ............................ | 424/484 |
| 2005/0020506 A1 | 1/2005 | Drapeau et al. | |
| 2007/0224245 A1 * | 9/2007 | Ameer .................... | A61L 27/12 424/426 |
| 2009/0253810 A1 * | 10/2009 | Katz ...................... | A61K 35/32 514/773 |

FOREIGN PATENT DOCUMENTS

| | | |
|---|---|---|
| JP | 2002-501786 A | 1/2002 |
| JP | 2003-088579 A | 3/2003 |
| JP | 2003-516730 A | 5/2003 |
| JP | 2006-522670 A | 10/2006 |
| JP | 2007-500043 A | 1/2007 |
| JP | 2007-526085 A | 9/2007 |

(Continued)

*Primary Examiner* — Yashita Sharma
(74) *Attorney, Agent, or Firm* — Jordan IP Law, LLC; Todd A. Vaughn

(57) ABSTRACT

A bone implant matrix for human or veterinary use, the matrix including a base matrix either treated or to be treated with a reinforcing mixture containing at least a polymer. The bone implant matrix is particularly adapted for use in bone reconstructive surgery, maxillo-facial bone reconstructive surgery and oral surgery.

8 Claims, 3 Drawing Sheets

(56) References Cited

FOREIGN PATENT DOCUMENTS

Figure 1:
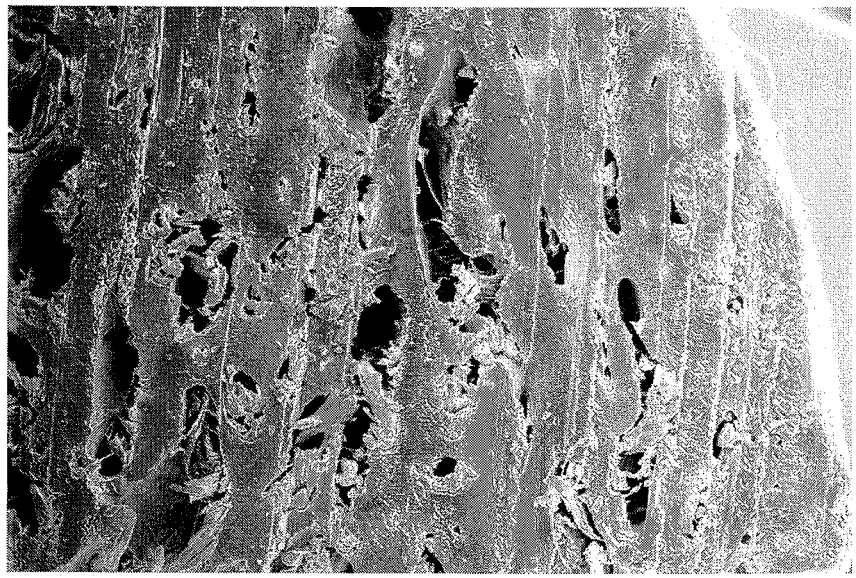

| WO | WO 97/46178 | 12/1997 |
| WO | 9938543 A2 | 8/1999 |
| WO | 0134801 A2 | 5/2001 |
| WO | 2004091435 A1 | 10/2004 |
| WO | WO 2004/098456 | 11/2004 |
| WO | 2005084725 A1 | 9/2005 |
| WO | WO 2008/088117 | 7/2008 |

* cited by examiner

BONE IMPLANT MATRIX AND METHOD OF PREPARING THE SAME

CROSS REFERENCE TO PRIOR APPLICATIONS

The present application is a National Stage Application of PCT International Application No. PCT/IB2009/007759 (filed on Dec. 15, 2009), under 35 U.S.C. 371, which claims priority to Swiss Patent Application No. 01997/08 (filed on Dec. 19, 2008), each of which are hereby incorporated by reference in their respective entireties.

FIELD OF THE INVENTION

The present invention relates to implant matrixes to be used generally in the bone reconstructive surgery field, in orthopaedics, and in particular, in oral surgery, dental implantology and maxillo-facial implantology.

BACKGROUND

The weakness of bone structure is a well-known condition to all surgeons in the orthopaedic field, in particular in the maxillo-facial and dental field. The causes are of several kinds, but quite well-known and understood. As regards means available to improve and reinforce the bones, it can be stated, that a wide variety of solutions have been proposed. Indeed, a number of techniques are currently available in the state of the art, which might be briefly distinguished in the following types: a) injections into target bone or cements or other mixtures; b) reinforcement with artificial supports to be added aside bone, being said supports metallic or polymeric o ceramic; c) tissue engineering, an approach wherein grafts are used that are made of osteoconductive and osteoinductive materials, such as e.g., some bioglasses; d) regenerative medicine, where artificial matrixes are used in order to host and deliver living cells to target area and thus enhance the formation of new resistant bone.

The introduction of new implant materials has allowed a remarkable development in bone reparative and reconstructive surgery in the last decades. Choosing an implant material is based on the osteogenesis, osteoinduction and osteoconduction properties of the material thereof. The most efficient solution among those currently available is to use an autologous bone as implant material, which implies, however, some disadvantages and risks. The quantity of material available to prepare the implant is limited and moreover the patient must undergo a dual intervention, the first for removing autologous bone and the second for the subsequent implant.

In accordance with the currently available techniques, an alternative way is represented by the usage of homologous tissue, that is the usage of demineralised bone matrix (DBM). The DBM is obtainable by a living donor or by a donor corpse. The human cortical derived DBM, however, has the same drawback of the autologous bone, i.e. the quantity of available material appears to be reduced. Further risks exist connected to possible infections, in particular viral and to potential compatibility problems, since the material to be implanted is of a heterologous nature. Moreover, the psychological aspect for the recipient, above all when the material is corpse-derived, represents an unnegligible critical element.

As it is known in the state of the art, as an alternative, the DBM may be of animal origin, in particular bovine. In the latter case, however, a microscopic examination can show that the bovine DBM porosity is higher than the cortical-derived human DBM, with a resulting minor compatibility and a reduced predisposition to the cell rooting and the growth of new integrated functional tissue.

The Applicant has observed that the higher porosity and the chemical structure of the bovine DBM result into a lower mechanical resistance, with a consequent higher weakness thereof. Such a weakness is particularly disadvantageous both in the pre-implant step, since shaping the matrix, according to the shape of the bone cavity which will host the matrix itself, with the desired accuracy is not easy, and in the implant in situ positioning step, because of the poor toughness of the matrix itself, which is often subject to a fragile fracture during the clamping steps.

Moreover, just because of the material weakness, the positioning and insertion of clamping elements (for example, screws) in such a matrix, is difficult and not enough accurate and, as stated before, it often causes the matrix break. Even further, during the shaping step of the matrix currently available in the state of the art, such as, for example, demineralised bone matrixes, bioglasses, bio-ceramics, etc., disadvantageously, undesirable powders are formed. For example, in dentistry, the shaping step takes place just before the implantation and the resulting powders creep up also on the matrix to be implanted.

Another proposed solution is a composite osteoimplant described in U.S. Patent Publication No. 2008/0063684. Such an osteoimplant includes a polymer and bone-derived particles. The composite is adapted and constructed to be formable during or immediately prior to implantation and to be set after final surgical placement.

U.S. Pat. No. 7,270,813 describes a method for preparing bone-derived composites, wherein the mineral portion of the bone is treated with a coupling agent before being incorporated into a biocompatible polymeric matrix. The resulting composite may be used as such that or be further processed to form an osteoimplant.

Therefore, there is the need in the field of regenerative bone surgery to find new bone implant matrixes, which have satisfactory characteristics of mechanical resistance and ductility to tri-dimensional processing.

SUMMARY

Embodiments are related to a matrix for bone implant for human or veterinary use, the matrix including a base matrix either treated or to be treated with a mixture containing at least a polymer.

In accordance with embodiments, the base matrix can be composed of a synthetic material, such as, for example, one of a polymeric, metallic, ceramic, bio-ceramic and bio-glass.

In accordance with embodiments, the base matrix can be composed of an organic material, such as, for example, one of a demineralised bone matrixes, non-demineralised bone matrixes, natural polymeric matrixes and mineral matrixes.

In accordance with embodiments, the base matrix and/or the polymer of the reinforcing mixture is bio-integrable.

In accordance with embodiments, the base matrix is a bone demineralised or non-demineralised, bovine or human corpse-derived matrix.

In accordance with embodiments, the base matrix is polymeric of biocompatible polymers.

In accordance with embodiments, the polymer of the reinforcing mixture is one of a biodegradable polymers, non-biodegradable polymers, co-polymers of biodegradable polymers, co-polymers of non-biodegradable polymers, co-polymers of biodegradable and non-biodegradable polymers.

In accordance with embodiments, the biodegradable polymer is one of poly(arylates), poly(acrylates), poly(anhydrides), poli(hydroxyacids), polyesters, poly(orthoesters), polycarbonates, poly(propylene fumarates), poly(amide esters), poly(amide carbonates), polyamides, polyaminoacids, polyacetals, polylactides, polyglycolides, poly(dioxanones), polyhydroxybutyrate, polyhydroxyvalerate, poly vinyl pyrrolidone, polycyanoacrylates, polyurethanes, polyalkylene oxides, polyamino carbonates, polyester amides, polyester imides, polyarylate aminoacids, polycarbonate aminoacids, polysaccharides, poly-ethylene-glycole and tyrosine-based polymers including polyarilates, polyacrylates and polycarbonates.

In accordance with embodiments, the bio-degradable polyester is one of a polylactic acid (PLA), poliglycolic acid (PGA), polycaprolactone (PCL) and co-polymers thereof including polycaprolactone-polylactic (PLA/PCL) co-polymers and poly(L-lactide-co-ϵ-capcolactone) co-polymers.

In accordance with embodiments, the non-biodegradable polymer is one of a polypyrrole, polyaniline, polythiophene and derivates thereof, polystyrene, polyurethanes, polyureas, poly(ethylenevinylacetate), polypropylene, polymethacrilate, polyethylene and poly(ethylene oxide).

In accordance with embodiments, the polymer is one of a starch, poly(caprolactones), poly(L-lactide), poly(D,L-lactide-co-glycolide), poly(L-lactide-co-D,L-lactide), their enantiomers, their co-polymers and mixtures thereof.

In accordance with embodiments, the reinforcing mixture includes an additive such as, for example, one of cell-nutrients, cell-growth promoters, cell-adhesion promoters, osteo-inductors, osteo-integrators, and "friendliness to cell."

In accordance with embodiments, the "friendliness to cell" is one of gelatine, hydrolysed gelatine, glycosaminoglycanes, polysaccharides, agarose, dextrane, chitosane, fibrin, fibrinogen and derivates thereof, collagen of any kind and derivates thereof, hyaluronic acid and derivates thereof, vitamins, comprising vitamin D, soya-isoflavons comprising genestein, drugs, which reduce the bone destruction and stimulate the bone reconstruction including strontium ranelate.

In accordance with embodiments, the reinforcing mixture includes at least a biodegradable polyester and at least a "friendliness to cell."

In accordance with embodiments, the bone implant matrix can also include a bovine demineralised bone matrix treated with a reinforcing mixture including a biodegradable polyester-based co-polymer and hydrolysed gelatine.

In accordance with embodiments, the biodegradable polyester-based co-polymer is a polycaprolactone-polylactic copolymer (PLA/PCL).

In accordance with embodiments, the biodegradable polyester-based co-polymer is a poly(L-lactide-co-ϵ-caprolactone) co-polymer.

The bone implant matrix object of the present invention is suitable to be used in the bone reconstructive surgery field in general, in orthopaedics and in particular in the oral surgery, in the maxillo-facial and dental implantology.

Embodiments are related to the use of the bone implant matrix in bone reconstructive surgery, such as, for example, maxillo-facial bone reconstructive surgery and oral surgery.

Embodiments are related to a method for preparing a bone implant matrix that includes at least the following: preparing a solution of a reinforcing mixture containing at least a polymer, deeping a base matrix into said reinforcing mixture solution, drying and optionally degassing the matrix for removing possible solvent residues.

In accordance with embodiments, the method can optionally include a post-treatment, such as, for example, heating, conditioning in an inert atmosphere and vacuum degassing.

In accordance with embodiments, the method can optionally include packaging in sterile and inert atmosphere, and sterilization.

DRAWINGS

Particular embodiments of the invention are described in detail herein below, as a way of example and not limited to, with reference to the attached figures, which illustrate at least the following by way of example.

Example FIG. 1 illustrates an optical microscopy image of the cortical layer of human bone.

Figure 2:
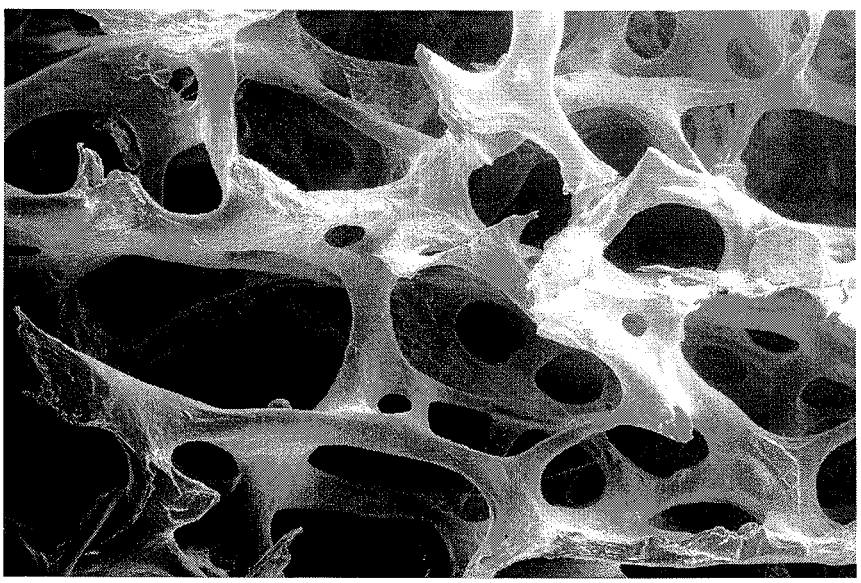

Example FIG. 2 illustrates an optical microscope image of a bovine-derived purified bone.

Figure 3:
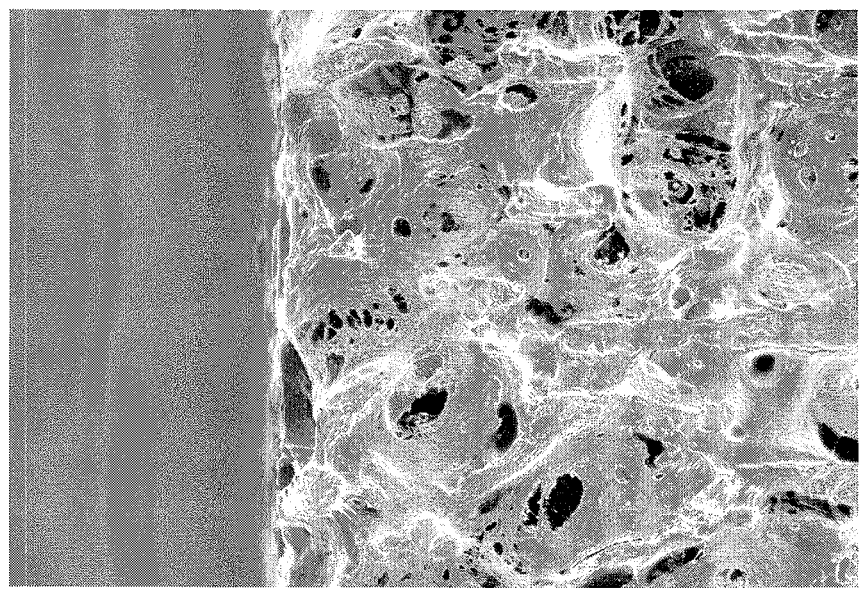

Example FIG. 3 illustrates an optical microscope image of a bovine-derived bone reinforced in accordance with embodiments of the invention.

Figure 4:
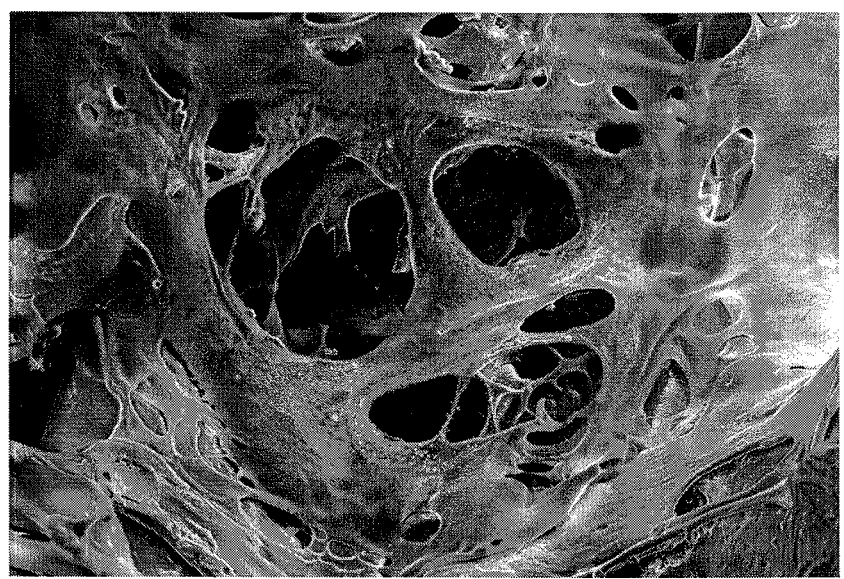

Example FIG. 4 illustrates a scanning electronic microscope (SEM) image of a section of a bone implant matrix made in accordance with embodiments of the invention which subsequently underwent a cell seeding, with chondrocyte-type cells, though the micro-seeding technique. The image was obtained on the third day after the seeding.

Figure 5:
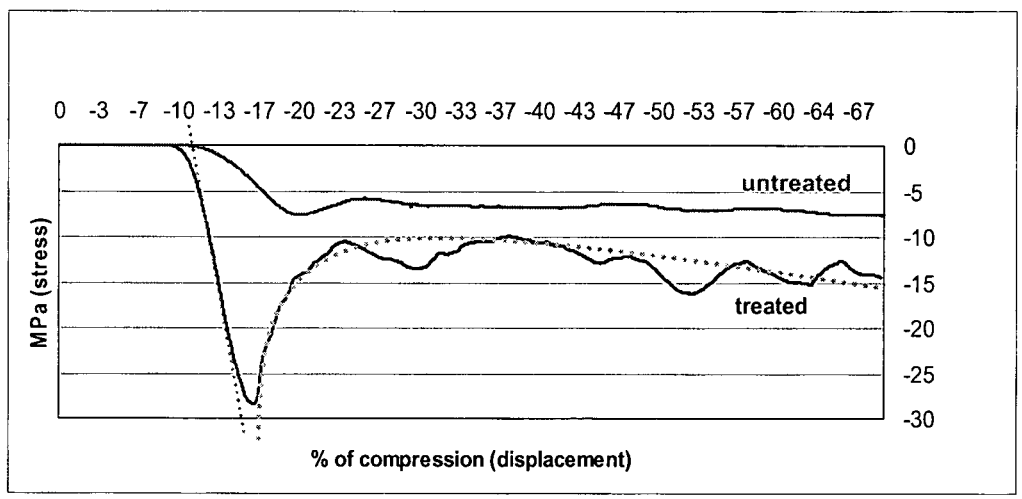

Example FIG. 5 illustrates a chart of two graphs showing monaxial mechanical crushing strength of an untreated bovine-derived matrix and a matrix treated with a reinforcing mixture in accordance with embodiments.

DESCRIPTION

A bone implant matrix in accordance with embodiments of the invention includes a base matrix which is actually treated or will be treated with a reinforcing mixture containing at least a polymer. By the expression "base matrix," a substantially solid tri-dimensional body is meant, intended after a treatment described hereinbelow, to be implanted in bone cavities. Moreover, by the expression "reinforcing mixture" it is meant a mixture including at least a polymer, i.e., which includes only one polymer or, alternatively, it may be multi-polymeric, i.e., may include more than one polymer at the same time. In particular, by the expression "reinforcing mixture" it is meant a mixture, such that the synthetic or natural material(s), and advantageously bio-compatible, polymer(s), are finely dispersed.

The base matrix may be composed of synthetic or natural materials. The synthetic base matrixes may be, for example, polymeric, metallic, ceramic, bio-ceramic, bio-glass matrixes. The polymeric type synthetic base matrix are preferred, in particular of bio-compatible polymers. The base matrix and the polymer(s) of the reinforcing mixture are advantageously bio-compatible. Furthermore, the base matrix and/or the polymer of the reinforcing mixture are preferably bio-integrable, in order to better assist the growth of the new bone integrated with the surrounding tissue.

Whereas, the natural base matrixes may be selected, for example, from demineralised bone, non-demineralised bone, natural polymeric, mineral matrixes. Among the natural base matrixes which may be used for carrying out the present invention, the human corpse-derived bone matrixes are preferred and the animal-derived demineralised or non-demineralised bone matrixes are particularly preferred, in particular, preferably, bovine. The bone implant matrixes may have different shapes and dimensions, such as to be adapted according to the shape and the dimensions of the bone cavities, where said matrixes can be implanted. For example, such bone matrixes may be parallelepiped-shaped, in particular cube-shaped. The dimensions of the bone implant matrixes, for example, can vary from a few mm till some dm of maximum length.

Particularly preferred is a reinforcing mixture obtained starting from two solutions, each of a soluble polymer respectively, immiscible to each other and made partially miscible by adding an alcohol or another proper solvent; in order to obtain a fine polymer dispersion, which, during the solvent evaporation step causes a homogeneous and finely dispersed coating. The polymer of the reinforcing mixture may be selected, for example, from the group consisting of biodegradable polymers, non-biodegradable polymers, co-polymers of the biodegradable polymers, co-polymers of the non-biodegradable polymers, co-polymers of the biodegradable and non-biodegradable polymers. In particular, the biodegradable polymers are selected from poly(arylates), poly(acrylates), poly(anhydrides), poli(hydroxyacids), polyesters, poly(orthoesters), polycarbonates, poly(propylene fumarates), poly(amide esters), poly(amide carbonates), polyamides, polyaminoacids, polyacetals, polylactides, polyglycolides, poly(dioxanones), polyhydroxybutyrate, polyhydroxyvalerate, polyvinyl pyrrolidone, polycyanoacrylates, polyurethanes, polyalkylene oxides, polyamino carbonates, polyester amides, polyester imides, aminoacid polyarylates, aminoacid polycarbonates, polysaccharides, poly-ethylene-glycole and tyrosine-based polymers, comprising polyarilates, polyacrylates and polycarbonates.

Among the biodegradable polymers, polyesters are preferred, in particular polylactic acid (PLA), polyglycolic acid (PGA), polycaprolactone (PCL) and co-polymers thereof, such as, for example, polycaprolactone-polylactic (PLA/PCL) co-polymers and poly(L-lactide-co-ϵ-capcolactone) co-polymers.

Regarding non-biodegradable polymers, these may be selected from polypyrrole, polyanilines, polythiophene and derivates thereof, polystyrene, polyurethanes, polyureas, poly(ethylenevinylacetate), polypropylene, polymethacrylate, polyethylene, poly(ethylene oxide). Moreover the polymer may be selected from the group comprising starch, poly(caprolactones), poly(L-lactide), poly(D,L-lactide-co-glycolide), poly(L-lactide-co-D,L-lactide), their enantiomers, their co-polymers and mixtures thereof.

In accordance with embodiments of the invention, the reinforcing mixture may include, beside the polymer or polymers, at least an additional component selected from cell nutrients, cell-growth promoters, cell-adhesion promoters, osteoinductors, osteointegrators, "friendliness to cell." By the expression "friendliness to cell" it is meant a substance, which is able to promote the cell-rooting and the cell growth, by stimulating cell proliferation and tissue integration.

In accordance with embodiments of the invention, the "friendliness to cell" may be selected from the group consisting of glycosaminoglycanes; polysaccharides including agarose, dextrane, chitosane; fibrin, fibrinogen and derivates thereof; collagen of any kind and derivates thereof; hyaluronic acid and derivates thereof; vitamins, such as vitamin D; soya-isoflavons including genestein; drugs, which reduce the bone destruction and stimulate the bone reconstruction, for example, drugs used in treating the osteoporosis including strontium ranelate and the use of gelatine, in particular hydrolysed, as "friendliness to cell" is particularly preferred. The presence of at least one "friendliness to cell" assists the cell rooting and growth, since the cell proliferation and the tissue integration are promoted and this is an important advantage over the prior art.

The solvents used to prepare the reinforcing mixture are commonly known in the state of the art and may be, for instance, dichloromethane, tetrahydrofuran, isopropanol, etc.

A particularly preferred embodiment of the bone implant matrix includes a base matrix, which is a bovine demineralised bone matrix treated with a reinforcing mixture including a biodegradable polyester-based co-polymer, such as, for example, a polycaprolactone-polylactic co-polymer (PLA/PCL) and, preferably hydrolysed and gelatine.

In accordance with embodiments of the invention, the bone implant matrix includes a base matrix, which is a bovine demineralised bone matrix treated with a reinforcing mixture including a biodegradable polyester-based co-polymer, such as, for example, a poly(L-lactide-co-ϵ-caprolactone), and preferably hydrolysed and gelatine.

In accordance with embodiments of the invention, the reinforcing mixture includes at least a biodegradable polyester and at least a "friendliness to cell."

In accordance with embodiments of the invention, a kit may be realized, and includes a reinforcing mixture in a proper separate container and the base matrix to be treated.

In accordance with embodiments of the invention, the bone implant matrix described herein may be used in the oral surgery, the bone reconstructive surgery and implantology. Such bone implant matrixes are particularly suitable to be used in oral surgery, in maxillo-facial and dental bone reconstructive surgery, in particular to reconstruct and consolidate the bone structures before carrying out the insertion of dental implants.

In accordance with embodiments of the invention, the bone implant matrixes are particularly suitable in the bone reconstructive surgery, following the decrease in the bone mass in patients affected by osteoporosis. Additionally, such bone implant matrixes may be used also in oral and dental applications, dentistry, as bone chips, as support matrixes for cell housing and in cellular therapies. The bone implant matrixes may be used for both human and veterinary use.

In accordance with embodiments of the invention, a method for preparing bone implant matrixes includes a) preparing a solution of a reinforcing mixture containing at least a polymer, b) dipping a base matrix into the reinforcing mixture made in accordance with step a), and then c) drying and degassing the matrix made in accordance with step b), preferably in a vacuum furnace at 37° C. (±2° C.) for 24 hours, for removing possible solvent residues (for example, in air or preferably in a vacuum furnace). Drying and degassing the bone implant matrix usually take place contemporarily. Such a method may optionally be followed by a post-treatment step, which can include, for example, heating, conditioning in a inert atmosphere the bone implant matrixes and degassing to remove completely the possible residues of solvents used in the preparation process.

Moreover, the bone implant matrix preparation process may be followed by a packaging method which includes the steps of d) packaging in a sterile and inert atmosphere, and then e) sterilization (preferably through gamma-ray irradiation).

The matrixes known in the state of the art and commonly used in the orthopaedic surgery have poor mechanical resistance and ductility characteristics.

Applicant has found that, by treating a base matrix with a reinforcing mixture containing at least a polymer, as described herein, it is possible to obtain bone implant matrixes which have such ductility characteristics as to make easier shaping the bone implant matrix in the pre-implant step, with the desired accuracy in relation to the bone cavity, which will host the matrix itself. Moreover, the mechanical resistance of the bone implant matrixes, obtainable in accordance with embodiments, determines a reduced trend to the fragile fracture of the matrixes themselves, this is particularly advantageous both in the implant in situ positioning step and in the positioning and insertion of clamping elements (for example, screws), of such a matrix.

The bone implant matrixes may be subject, during the pre-implant step, to a possible cell-seeding process. The cells can be seeded by using seeding techniques known in the state of the art, preferably with micro-seeding technique after the matrix has been brought to a temperature of 37° C. (preferably in an incubator). The seeded bone implant matrix is then covered with a proper culturing medium and kept inside the incubator in accordance with the techniques commonly required by the cell type used. For each centimeter of the bone implant matrix, the cell optimal load is about 300000-500000 cell/cm$^3$.

Example FIG. 4 illustrates how the bone implant matrix in accordance with embodiments of the invention allows the cell rooting, due to the porosity characteristics, in terms of both dimensions and available spaces. The presence of a lattice formed by the chondrocytes inside the porous spaces of the matrix is, indeed, pointed out. The following, not limitative, examples describe embodiments of the invention.

Embodiment Example 1

In accordance with embodiments of the invention, a method for preparing a bone implant matrix includes: preparing a solution that includes 1 g of polymer and 20 ml of dichloromethane, preparing 20 ml of 1.5% solution of hydrolysed porcine gelatine, adding 10 ml of isopropanol to the polymer solution previously prepared, stirring the obtained polymer solution for 15 minutes, adding the previously prepared porcine gelatine to the polymer solution, stirring the polymer solution so obtained for at least 5 minutes, dipping the base matrix into the polymer solution and keeping in immersion for at least 30 minutes, and then drying the product in the air for at least 24 hours. Optionally, the product may be treated subsequently in a furnace to remove the remaining solvent from the bone implant matrix (T<40° C.).

Embodiment Example 2

In accordance with embodiments of the invention, a method for preparing a bone implant matrix includes: preparing a solution that includes 1 g PLA/PCL co-polymer in 20 ml of dichloromethane, stirring at about 100 rpm the previously prepared solution with a magnetic stirrer for at least 45 minutes at room temperature, preparing 20 ml of 1.5% solution of hydrolysed porcine gelatine, injecting water to the previously prepared solution while gently stirring to add hydrolysed porcine gelatine, stirring at about 100 rpm the previously prepared solution for at least 1 hour at 37° C. (±2° C.), adding 10 ml of isopropanol to the PLA/PCL co-polymer solution in the previously prepared dichloromethane, stirring the previously prepared polymer solution for 20 minutes, adding the previously prepared gelatine solution to the co-polymer solution, stirring at about 180 rpm the polymeric solution so obtained for 10 minutes at room temperature, dipping a demineralised bone matrix into the polymer solution and keep in immersion for at least 30 minutes under stirring at about 200 rpm, and then inserting the product in a vacuum furnace for at least 24 hours at 37° C. (±2° C.).

Example 3

Experimental tests was conducted via optical microscope scanning of several substrates, using the ESEM system Evo 50 EP by Zeiss-Cambridge Instruments (Germany). All the images were obtained with the same magnitude: 30×. Moreover, all the images were normalised at the same proportions.

Example FIG. 1 illustrates an image obtained by the optical microscope of a human bone cortical layer, which presents the desirable porosity and mechanical resistance characteristics. Example FIG. 2 illustrates an image obtained by an optical microscope of a bovine demineralised bone matrix.

As illustrated in example FIG. 1, in the microscopic structure, remarkable differences may be highlighted in respect to the human bone cortical layer, in particular concerning the porosity. The latter appears much higher and poorly compatible with the cell rooting.

As illustrated in example FIG. 2, the bovine demineralised bone matrix, which represents a "base matrix" in accordance with embodiments of the invention, underwent a treatment with a reinforcing mixture containing at least a polymer, in particular containing a polycaprolactone-polylactic co-polymer (PLA/PCL) and hydrolysed gelatine.

As illustrated in example FIG. 3, an image of the reinforced bovine demineralised bone matrix obtained by the optical microscope is shown. As it can be seen by comparing example FIG. 1 and example FIG. 3, the microscopic structure of the bone implant matrix in example FIG. 3 obtained in accordance with embodiments of the invention shows strong similarity to the human bone cortical layer. In particular, concerning the porosity, which appears completely comparable in terms of both dimensions and available spaces for the cell rooting. The preliminary mechanical and pre-implant tests have confirmed an adequacy of the matrix shown in example FIG. 3 in implantology for human use, the behaviour of such a matrix is particularly satisfactory, if compared to the behaviour of the human bone cortical layer.

Although embodiments have been described herein, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method for preparing a bone implant matrix, the method comprising:
preparing a solution of a reinforcing mixture as a homogeneous and finely dispersing coating, said reinforcing mixture containing at least a polymer, and at least an additional component selected from a "friendliness to cell:" a substance which promotes cell-rooting and cell growth by stimulating cell proliferation and tissue integration, wherein the base matrix is a bone demineralised or non-demineralised, bovine corpse-derived matrix, the polymer of the reinforcing mixture is a biodegradable polyester selected from the group consisting of polylactic acid (PLA), poliglycolic acid (PGA), polycaprolactone (PCL) and co-polymers thereof comprising polycaprolactone-polylactic (PLA/PCL) co-polymers and poly(L-lactide-co-ϵ-capcolactone) co-polymers, poly(Llactide), poly(D,L-lactide-co-glycolide), poly(L-lactide-co-D,L-lactide), their enantiomers, their co-polymers and mixtures thereof, and the "friendliness to cell" is selected from the group consisting of gelatine, and hydrolysed gelatin, at least a polymer and at least an additional component selected from cell nutrients, cell-growth promoters, cell-adhesion promoters, osteo-inductors, osteo-integrators, "friendliness to cell:" a substance, which promotes cell-rooting and cell growth by stimulating cell proliferation and tissue integration, starting from two solutions, each solution made of a soluble polymer and an additional component, and which are immiscible to each other, but made partially miscible by adding an alcohol or another solvent respectively therein in order to obtain a fine polymer dispersion;

dipping a base matrix into said reinforcing mixture solution; and then removing solvent residues from the bone implant matrix by at least one of drying and degassing the bone implant matrix.

2. The method of claim 1, further comprising:

one of heating, conditioning in an inert atmosphere and vacuum degassing the bone implant matrix.

3. The method of claim 1, further comprising, after removing the solvent residues from the bone implant matrix:

packaging the bone implant matrix in a sterile and inert atmosphere; and then sterilizing the bone implant matrix.

4. A bone implant matrix comprising:

a base matrix treated with a reinforcing mixture as a homogeneous and finely dispersing coating, said reinforcing mixture containing at least a polymer, and at least an additional component selected from a "friendliness to cell:" a substance which promotes cell-rooting and cell growth by stimulating cell proliferation and tissue integration, wherein the base matrix is a bone demineralised or non-demineralised, bovine corpse-derived matrix, the polymer of the reinforcing mixture is a biodegradable polyester selected from the group consisting of polylactic acid (PLA), poliglycolic acid (PGA), polycaprolactone (PCL) and co-polymers thereof comprising polycaprolactone-polylactic (PLA/PCL) co-polymers and poly(L-lactide-co-ϵcapcolactone) co-polymers, poly(Llactide), poly(D,L-lactide-co-glycolide), poly(L-lactideco-D,L-lactide), their enantiomers, their co-polymers and mixtures thereof, the "friendliness to cell" is selected from the group consisting of gelatine, and hydrolysed gelatin, wherein the reinforcing mixture is obtained starting from two solutions, each of the solutions made of a soluble polymer comprising a biodegradable polyester, and an additional component comprising the gelatine or the hydrolysed gelatine, respectively, immiscible to each other, but made partially miscible by adding an alcohol or another proper solvent in order to obtain a fine polymer dispersion.

5. The bone implant matrix of claim 4, wherein the base matrix is a bone, non-demineralised, bovine corpse-derived matrix.

6. The bone implant matrix of claim 4, wherein the reinforcing mixture comprises a biodegradable polyester-based co-polymer and hydrolysed gelatine, wherein the biodegradable polyester-based co-polymer is selected from the group consisting of polycaprolactone-polylactic copolymer (PLA/PCL) and poly(L-lactide-co-ϵ-caprolactone) copolymer.

7. The bone implant matrix of claim 4, wherein the bone implant matrix is adapted for use in bone reconstructive surgery, maxillo-facial bone reconstructive surgery, oral surgery, dental surgery and implantology.

8. The bone implant matrix of claim 4, wherein the bone implant matrix is adapted for human and veterinary use.

\* \* \* \* \*